United States Patent [19]

Bajusz et al.

[11] Patent Number: 4,703,036

[45] Date of Patent: Oct. 27, 1987

[54] PEPTIDE-ALDEHYDES, PROCESS FOR THE PREPARATION THEREOF AND PHARMACEUTICAL COMPOSITIONS CONTAINING THE SAME

[75] Inventors: Sándor Bajusz; Erzsbet Szell nee Hasenöhrl; Daniel Bagdy; Eva Barabas, all of Budapest; Mariann Dioszegi, Kerepestarcsa; Zsuzsa Fittler, Budapest; Ferencz Jozsa, Budapest; Gyula Horvath, Budapest; Eva Tomori nee Jozst, Budapest, all of Hungary

[73] Assignee: Richter Gedeon Vegyeszeti Gyar RT, Budapest, Hungary

[21] Appl. No.: 811,937

[22] Filed: Dec. 20, 1985

[30] Foreign Application Priority Data

Dec. 21, 1984 [HU] Hungary ................ 4763/84

[51] Int. Cl.⁴ ................ A61K 37/43; C07K 5/08
[52] U.S. Cl. ................ 514/18; 530/331
[58] Field of Search ................ 530/331; 514/18

[56] References Cited

U.S. PATENT DOCUMENTS 4,399,065  8/1983  Bajusz et al. ................ 530/331
4,478,745 10/1984  Bajusz et al. ................ 530/331

*Primary Examiner*—Delbert R. Phillips

*Attorney, Agent, or Firm*—Karl F. Ross; Herbert Dubno; Jonathan Myers

[57] ABSTRACT

The invention relates to new peptide-aldehydes and a process for the preparation thereof, furthermore to pharmaceutical compositions containing the same.

According to a feature of the present invention there are provided new peptide-aldehyde derivatives corresponding to the general formula (I)

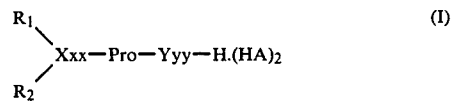

wherein
 $R_1$ represents hydrogen or $C_{1-6}$ alkyl group,
 $R_2$ stands for $C_{1-6}$ alkyl group, furthermore $R_1$ and $R_2$ are linked to the amino group of the Xxx alpha-amino acid,
 Xxx represents a D-phenylalanine residue or a D-alpha-amino acid group having in the side chain a $C_{1-4}$ alkyl group,
 Pro stands for L-proline residue,
 Yyy stands for L-, D- or DL-arginine residue and
 A represents an acid residue.

The new peptide-aldehyde derivatives of the invention possess valuable anticoagulant activity.

10 Claims, No Drawings

PEPTIDE-ALDEHYDES, PROCESS FOR THE PREPARATION THEREOF AND PHARMACEUTICAL COMPOSITIONS CONTAINING THE SAME

FIELD OF THE INVENTION

This invention relates to new peptide-aldehydes and a process for the preparation thereof, furthermore to pharmaceutical compositions containing the same.

According to a feature of the present invention there are provided new peptide-aldehyde derivatives of the formula (I),

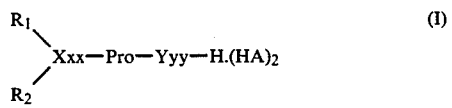

wherein $R_1$ represents hydrogen or $C_{1-6}$ alkyl group, $R_2$ stands for $C_{1-6}$ alkyl group, furthermore $R_1$ and $R_2$ are linked to the amino group of the Xxx alpha-amino acid, Xxx represents a D-phenylalanine residue or a D-alpha-amino acid group having a $C_{1-4}$ alkyl group in the side chain, Pro stands for L-proline residue, Yyy stands for L-, D- or DL-arginine residue and A represents an acid residue.

In the foregoing definition the term "$C_{1-6}$ alkyl" covers straight or branched alkyl groups, e.g. methyl, ethyl, n-propyl, isopropyl, n-butyl, isobutyl, n-hexyl, etc.

Preferred representatives of the compounds having the formula (I) are those described in the Examples.

Particularly preferred representatives of the compounds according to the invention are the following derivatives:

N-methyl-D-phenylalanyl-L-prolyl-L-arginine-aldehyde sulfate,

N,N-dimethyl-D-phenylalanyl-L-prolyl-L-arginine-aldehyde sulfate,

N-ethyl-D-phenylalanyl-L-prolyl-L-arginine-aldehyde sulfate,

N-isobutyl-D-phenylalanyl-L-prolyl-L-arginine-aldehyde sulfate,

N-methyl-D-alloisoleucyl-L-prolyl-L-arginine-aldehyde sulfate, and N-n-hexyl-D-phenylalanyl-L-prolyl-L-arginine-aldehyde sulfate.

BACKGROUND OF THE INVENTION

It is known that both the blood clotting process and the lysis of the blood clots are results of a proteolytic reaction. In the process of blood clotting the thrombin-fibrinogen reaction represents the key step wherein the fibrinogen, dissolved in the blood plasma, is converted into the insoluble fibrin polymer, whereas in the lypis process the fibrin polymer is cleaved into soluble fragments by the proteolytic action of plasmin. Good anticoagulants applicable in therapy are expected to inhibit the blood clotting process while permitting the plasmin-fibrin reaction (clot lysis) to proceed. Free tripeptide aldehyde salts of the structure D-phenylalanyl-L-prolyl-L-arginine-aldehyde (Hungarian patent specification No. 169,870 and Belgian patent specification No. 891,708) are anticoagulants possessing such properties. These compounds have no influence on the plasmin-fibrin reaction. In their presence, depending on their concentration, either no fibrin clot is formed or a loose one easily lysed by plasmin. However, it is also known that tripeptide-aldehydes, having a free amino terminal group, are rather unstable, rapidly losing their initial high enzyme inhibitory activity; only D-phenylalanyl-L-prolyl-L-arginine-aldehyde sulfate, described in Belgian patent specification No. 891,708, possesses significant stability, retaining its initial activity in cool solution (5° C.) for a prolonged period.

On testing the stability of D-phenylalanyl-L-prolyl-L-arginine-aldehyde sulfate at higher temperatures it was found that in aqueous solution, at 80° to 100° C., it was transformed within hours, while at 37° to 40° C. within 10 to 14 days practically completely into a stable tricyclic compound, devoid of enzyme inhibitory activity. The structure of this compound [1,2,4,5,6,6a-hexahydro-1-benzyl-2-oxo-8-(4'-guanidino)-butyl-pyrrolo[1,2-a]imidazolo[2,1-c]pyrazine] was confirmed by mass spectrometry and NMR spectroscopy. Though it was found that the corresponding acyl-tripeptide-aldehydes fail to undergo similar conversion, nevertheless the acyl derivatives, e.g. t-butyloxycarbonyl-D-phenylalanyl-L-prolyl-L-arginine-aldehyde hemisulfate, inhibit both the thrombin-fibrinogen and the plasmin-fibrin reaction [Belgian patent specification No. 891,708 and S. Bajusz et al., in Peptides, Synthesis-Structure-Function (Eds.: H. D. Rich and E. Gross) Pierce Chem. Co., Rockford, Ill., USA, p. 817], they are less suitable for anticoagulant therapy.

OBJECT OF THE INVENTION

It is the aim of the present invention to prepare novel peptide-aldehydes which possess the selective anticoagulant potency of D-phenylalanyl-L-prolyl-L-arginine-aldehyde sulfate but are more stable and not prone to irreversible cyclization.

DESCRIPTION OF THE INVENTION

It was unexpectedly found that tripeptide-aldehydes, alkylated at their terminal amino groups, i.e. N-methyl-, N-ethyl- or N-isobutyl-D-phenylalanyl-L-prolyl-L-arginine-aldehyde sulfate, fail to be irreversibly converted to the above-mentioned tricyclic compounds. During stability testing aqueous solutions of D-phenylalanyl-L-prolyl-L-arginine-aldehyde sulfate as well as of the corresponding N-alkyl derivatives with a concentration of 10 mg/ml (pH=6.0) were stored at 40° C. for 5 days. The transformations proceeding in the solutions were monitored by chromatography and by measuring antithrombin activity.

Thin-layer chromatography of D-phenylalanyl-L-prolyl-L-arginine-aldehyde sulfate on silica plates, using a developing solvent of ethyl acetate-pyridine-acetic acid-water (30:20:6:11) demonstrated the conversion process: the tripeptide-aldehyde spot ($R_F=0.40$) was gradually reduced at the simultaneous increase of the spot corresponding to the tricyclic compound ($R_F=0.6$), while in the chromatograms of the N-methyl, N-ethyl, N-isobutyl, and N,N-dimethyl derivatives no such conversion was detectable, solely the spots corresponding to the intact peptides were visible ($R_F=0.43$, 0.50, 0.64 and 0.37, respectively).

Furthermore it has also been found that diverse other salts of N-alkyl-tripeptide-aldehydes, i.e. acetates, similarly fail to be transformed into the corresponding tricyclic compounds while D-phenylalanyl-L-arginine-aldehyde acetate is especially highly susceptible to such conversions.

Antithrombin activities were assayed in a system containing the following components:
- 0.2 ml 0.5 percent bovine fibrinogen in a 0.9 percent solution of sodium chloride,
- 0.1 ml tris(hydroxymethyl)-amino-methane-hydrochloride-hydrochloric acid buffer (pH=7.2) containing the peptide solution, and
- 0.1 ml US Standard Human Thrombin (NIH, Bethesda, Md., USA), 10 unit/ml solution.

The clotting time of the peptide-free system is 15 s, measured in the "Schnither-Gross-Coagulometer". The initial activity of the tripeptide-aldehyde sulfates was arbitrarily set up as the mole concentration inducing the fivefold prolongation of clotting time in the system compared to the control ($I_{80}$ value). The activity of the peptides in the solutions, assayed on the 1st, 3rd and 5th day, was expressed as a percentage of the initial activity (zero day). The results were presented in Table 1.

- 0.1 ml tris(hydroxymethyl)-amino-methane hydrochloride-hydrochloric acid buffer (pH=7.2), containing the peptide,
- 0.1 ml 0.1 U plasmin dissolved in buffer solution (KABI, Stockholm, Sweden), and
- 0.1 ml US Standard Human Thrombin (NIH, Bethesda, Md., USA) 10 U/ml solution.

The lysis time of the fibrin gel formed in the peptide-free system is 10 minutes. D-Phenylalanyl-L-prolyl-L-arginine-aldehyde sulfate and the above-mentioned t-butyloxycarbonyl-D-phenylalanyl-L-prolyl-L-arginine-aldehyde hemisulfate were used as reference substances. The results were presented in Table 2.

The data demonstrate that the properties of N-alkyl-tripeptide-aldehydes are similar to those of the respective analogues with a free terminal amino group. In the presence of small amounts of the peptides the clot formed is lysed within the control period while in the presence of larger amounts either only a gel of rather loose structure is formed or no clot is produced at all.

TABLE 2

| Effect of tripeptide-aldehydes on the plasmin-fibrin reaction | | |
|---|---|---|
| Peptide-aldehyde | Peptide content $\mu M$ | Lysis time of fibrin clot* min. |
| N—Methyl-D-phenylalanyl-L-prolyl-L-arginine-aldehyde sulfate | 0.18 | 10 |
|  | 0.36 | ** |
|  | 0.72 | no clot formed |
| D-Phenylalanyl-L-prolyl-L-arginine-aldehyde sulfate (control) | 0.18 | 10 |
|  | 0.36 | ** |
|  | 0.72 | no clot formed |
| t-Butyloxycarbonyl-D-phenylalanyl-L-prolyl-L-arginine-aldehyde hemisulfate (control) | 0.18 | 10 |
|  | 0.36 | 20 |
|  | 0.72 | 40 |

*The lysis time of the fibrin gel formed in the peptide-free solution is 10 minutes
**No measurable lysis time due to clot of rather loose structure During the observation period D-phenylalanyl-L-prolyl-L-arginine-aldehyde sulfate lost more than 50 percent of its initial activity while the N-methyl derivative retained its initial potency, and the activity of the N-ethyl and N-isobutyl derivative was also reduced only by 15 to 20 percent. At the experimental conditions applied the incidence of partial racemization in the L-arginine-aldehyde terminal moiety is most probable, the slight reduction of activity can be attributed to this phenomenon.

However, the plasmin lysis time of the fibrin clot is dose-dependently increased by acyl-tripeptide-aldehyde hemisulfates.

The above experiments clearly demonstrate that the novel tripeptide-aldehydes alkylated on their N-terminal amino groups are significantly more stable than the known D-phenylalanyl-L-prolyl-L-arginine-aldehyde sulfate. They are good selective anticoagulants by inhibiting the thrombin-fibrinogen reaction while not interfering with the plasmin-fibrin reaction.

TABLE 1

| Change in the antithrombin activity of aqueous solutions of tripeptide-aldehyde sulfates stored at 40° C. (pH = 6.0) | | | | | |
|---|---|---|---|---|---|
|  | Initial activity | | Activity (%) | | |
| Peptide-aldehyde | $I_{80}, \mu M^*$ | (zero day) | Day 1 | Day 2 | Day 3 |
| N—Methyl-D-phenylalanyl-L-prolyl-D-arginine-aldehyde sulfate | 0.25 | (100%) | 100 | 100 | 100 |
| N—Ethyl-D-phenylalanyl-L-prolyl-L-arginine-aldehyde sulfate | 0.21 | (100%) | 100 | 100 | 85 |
| N—Isobutyl-D-phenylalanyl-L-prolyl-L-arginine-aldehyde sulfate | 0.31 | (100%) | 100 | 85 | 80 |
| D-Phenylalanyl-L-prolyl-L-arginine-aldehyde sulfate (control) | 0.25 | (100%) | 100 | 50 | 40 |

*Peptide concentration in the reaction mixture in $\mu$moles inducing a fivefold prolongation of clotting time in the system compared to the control The effect of N-alkyl-tripeptide-aldehydes on the plasmin-fibrin reaction was also studied and demonstrated on the example of N-methyl-D-phenylalanyl-L-prolyl-L-arginine-aldehyde sulfate in the following system:
- 0.2 ml 0.5 percent bovine fibrinogen in a 0.9 percent solution of sodium chloride, The novel N-alkyl-tripeptide-aldehydes of formula (I) also exhibit significant anticoagulant activity in vivo. The peptides, dissolved in isotonic saline solution, were administered orally or intravenously to male New Zealand rabbits weighing 2 to 3 kg. At intravenous application infusions of 0.5 to 2.0 mg/kg/h were given at a rate of 6 ml/h for 3 hours. At oral administration 20 to 30 mg/kg doses of the peptides were given in volumes of 2 ml. After application blood samples were taken in 30 minute periods from the ear vein of the rabbits and the clotting time of whole blood was assayed in a Thromboelastograph [H. Harter: Zeitschrift für klinische Medizin 153, 423 (1955)], simultaneously the plasma thrombin time was measured, too [R. T. S. Jim: J. Lab. Clin. Med. 50, 45 (1957)]. The lowest doses required to attain therapeutic effect (M. Verstraete and R. Verwilghen in Drug Treatment, 2nd ed., Ed.: G. S. Avery, Churchill Livingstone, Edinburgh-London, 1980, p. 919) were presented in Table 3, D-phenylalanyl-L-prolyl-L-arginine-aldehyde sulfate served as reference substance.

The data demonstrate that the efficacy of N-alkyl-tripeptide-aldehydes is similar or identical to that of the reference substance.

TABLE 3

In vivo anticoagulant effect of tripeptide aldehydes in male New Zealand rabbits

| Tripeptide-aldehyde | Lowest effective dose | |
| --- | --- | --- |
| | iv mg/kg/h | po mg/kg/h |
| N—Methyl-D-phenylalanyl-L-prolyl-L-arginine-aldehyde sulfate | 0.5 | 20 |
| N—Ethyl-D-phenylalanyl-L-prolyl-L-arginine-aldehyde sulfate | 0.5 | 20 |
| N—Isobutyl-D-phenylalanyl-L-prolyl-L-arginine-aldehyde sulfate | 0.5 | 20 |
| N,N—Dimethyl-D-phenylalanyl-L-prolyl-L-arginine-aldehyde sulfate | 2.0 | 30 |
| N—Methyl-D-alloisoleucyl-L-prolyl-L-arginine-aldehyde sulfate | 1.0 | 30 |
| D-Phenylalanyl-L-prolyl-L-arginine-aldehyde sulfate (control) | 0.5 | 20 |

On the basis of intravenous infusion trials in rabbits the dose of the human intravenous infusion was established as 1 to 2 mg/kg/h.

The N-alkyl-tripeptide-aldehydes of general formula (I) can be prepared by acylating the arginine lactam, protected at the guanidino group, with the N-terminal-dipeptide moiety as acyl component, the protected tripeptide-lactam formed is reduced to the protected tripeptide-aldehyde, the protecting groups are removed and the N-alkyl-tripeptide-aldehyde is isolated in the form of a salt.

According to a further feature of the present invention there is provided a process for the preparation of new tripeptide-aldehydes of formula (I), wherein $R_1$, $R_2$, Xxx, Pro, Yyy and A have the same meaning as above, characterized by condensing, by a method known in peptide chemistry, an arginine lactam, protected at its guanidino group, with an N-protected-N-monoalkyl-Xxx-Pro-OH or N,N-dialkyl-Xxx-Pro-OH dipeptide, the protected tripeptide lactam formed is reduced to the protected tripeptide-aldehyde, the protecting groups are removed and the resulting N-alkyl or N,N-dialkyl-tripeptide-aldehyde is isolated in the form of a salt.

The starting N-monoalkyl or N,N-dialkyl-Xxx-Pro-OH dipeptides are also new.

According to a further feature of the present invention there is provided a process for the preparation of the starting new N-monoalkyl or N,N-dialkyl-Xxx-Pro-OH dipeptides, characterized by condensing, by a method known in peptide chemistry, the Xxx amino acid, protected at the N-terminal amino group, with L-proline, and the resulting protected dipeptide is alkylated, or an Xxx-Pro-OH dipeptide, having a free amino terminal group, is mono- or dialkylated, or an Xxx amino acid, monoalkylated and protected or dialkylated at its amino group, is condensed by a method known in peptide chemistry, with L-proline.

According to a preferred embodiment of the process of the invention the N-benzyloxycarbonyl derivative of D-phenylalanyl-L-proline is methylated in the presence of sodium hydride with methyliodide, the obtained N-benzyloxycarbonyl-N-methyl-D-phenylalanyl-L-proline is condensed by the mixed anhydride method to L-arginine lactam, the resulting protected tripeptide lactam is reduced with lithium aluminium hydride to the N-benzyloxycarbonyl-N-methyl-D-phenylalanyl-L-prolyl-N$^\omega$-benzyloxycarbonyl-L-arginine-aldehyde.

The protecting groups are removed by hydrogenolysis in the presence of sulfuric acid and the resulting N-methyl-D-phenylalanyl-L-prolyl-L-arginine-aldehyde sulfate is isolated.

According to a further preferred embodiment of the process of the invention D-phenylalanyl-L-proline is submitted to hydrogenolysis in the presence of formaldehyde. The N,N-dimethyl-D-phenylalanyl-L-proline formed is condensed by the mixed anhydride method with N$^\omega$-benzyloxycarbonyl-L-arginine lactam, the resulting protected tripeptide lactam is reduced by lithium aluminum hydride to N,N-dimethyl-D-phenylalanyl-L-prolyl-L-arginine-aldehyde, the protecting groups are removed by hydrogenolysis in the presence of sulfuric acid and finally the N,N-dimethyl-D-phenylalanyl-L-prolyl-L-arginine-aldehyde sulfate is isolated.

According to a further embodiment of the present invention D-phenylalanine is submitted to hydrogenolysis in the presence of acetaldehyde, the resulting N-ethyl-D-phenylalanine is provided with a benzyloxycarbonyl protecting group, its 2,4,5-trichlorophenyl ester is formed, then it is condensed with L-proline. The N-benzyloxycarbonyl-N-ethyl-D-phenylalanyl-L-proline obtained is coupled by the mixed anhydride method to N$^\omega$-benzyloxycarbonyl-L-arginine lactam. The protected tripeptide lactam obtained is reduced by lithium aluminum hydride to N-benzyloxycarbonyl-N-ethyl-D-phenylalanyl-L-prolyl-N$^{\omega\text{-}benzyloxycarbonyl\text{-}L\text{-}arginine\text{-}alde}$-*hyde, the protecting groups are removed by hydrogenolysis in the presence of sulfuric acid and the resulting N-ethyl-D-phenylalanyl-L-prolyl-L-arginine-aldehyde sulfate is isolated.*

The products having D,L,L configuration, prepared in the above-mentioned way, may eventually contain a certain amount of a product having D,L,D configuration which, however, does not affect their therapeutic application.

In the acid addition salts of the peptides of formula (I) and of their derivatives as hereinabove recited the activity resides in the base, and the acid is of less importance although for therapeutic purposes it is preferably pharmacologically and pharmaceutically acceptable to the recipient. Examples of such suitable acids include (a) mineral acids: hydrochloric, hydrobromic, phosphoric, metaphosphoric, nitric and sulfuric acids, (b) organic acids: tartaric, acetic, citric, malic, lactic, fumaric, benzoic, glycolic, gluconic, gulonic, succinic and arylsulphonic, for example p-toluenesulphonic, acids. The pharmaceutically and pharmacologically acceptable acid addition salts together with those salts which are not so acceptable (for example salts of hydrofluoric and perchloric acids) have utility in isolation and purification of the bases and of course the unacceptable salts are also valuable in the preparation of the acceptable salts by techniques well known in the art. Those peptides and their derivatives containing a plurality of free amino groups may be obtained in the form of mono- or poly-acid addition salts, or as mixed salts of a plurality of acids.

According to a further feature of the present invention there are provided new pharmaceutical compositions containing as active ingredient at least one compound of formula (I) together with one or more pharmaceutical carriers, diluents and/or additives.

The pharmaceutical compositions can be prepared by methods generally applied in the pharmaceutical industry.

The invention is elucidated in detail by the aid of the following non-limiting Examples.

The $R_F$ values in the Examples are determined by silica gel thin-layer chromatography (Kieselgel G, Reanal, Budapest) in the following developing systems:
1. Ethyl acetate-pyridine-acetic acid-water-960:20:6:11
2. Ethyl acetate-pyridine-acetic acid-water-480:20:6:11
3. Ethyl acetate-pyridine-acetic acid-water-240:20:6:11
4. Ethyl acetate-pyridine-acetic acid-water-120:20:6:11
5. Ethyl acetate-pyridine-acetic acid-water-60:20:6:11
6. Ethyl acetate-pyridine-acetic acid-water-30:20:6:11

EXAMPLE 1

N-Methyl-D-phenylalanyl-L-prolyl-L-arginine-aldehyde sulfate

Step 1:
N-Benzyloxycarbonyl-N-methyl-D-phenylalanyl-L-prolyl-N$^\omega$-benzyloxycarbonyl-L-arginine lactam 42.95 g (0.11 mmole) of N-t-butyloxycarbonyl-N$^\omega$-benzyloxycarbonyl-L-arginine lactam are suspended in 110 ml of anhydrous chloroform, then at constant stirring 275 ml of a solution of hydrochloric acid in ethyl acetate (0.11 to 0.15 g/ml) are added. After stirring for 3 hours the reaction mixture is diluted with 400 ml of diethyl ether, the precipitated crystals are filtered, washed twice with 100 ml of diethyl ether and twice with 50 ml of acetone, then the product is dried in a vacuum desiccator in the presence of phosphorus pentoxide and potassium hydroxide. Following drying for about an hour the crystals are dissolved in 100 ml of dimethylformamide, cooled to −15° C. and at this temperature and at stirring first 20 ml, then further 10 to 15 ml of triethylamine are added to assure detectable excess of the base in the gaseous phase. The resulting suspension is added to the following mixed anhydride.

50.9 g (0.1 mole) of N-benzyloxycarbonyl-N-methyl-D-phenylalanyl-L-proline cyclohexylammonium salt are dissolved in 200 ml of diethyl ether and 120 ml of N sulfuric acid. The diethylether layer is washed three times with 30 ml of water each, dried over sodium sulfate and the solvent is evaporated from a water bath of 40° C. at a pressure of 25 to 30 millibar. The residue, together with 11.2 ml (0.1 mole) of N-methylmorpholine, is dissolved in 70 ml of dimethylformamide, cooled to −15° C., then at this temperature 13.2 ml (0.1 mole) of isobutyloxycarbonyl chloride are added. After completed addition stirring is continued for 5 minutes, then the above suspension in dimethylformamide is added to the mixed anhydride formed. The reaction mixture is stirred for one hour at −15° C., then for an other hour at 0° C., afterwards it is diluted with 200 ml of benzene and the precipitated salts are filtered. 150 ml of water are added to the benzene-dimethylformamide filtrate and the layers are separated. The lower aqueous dimethylformamide filtrate is extracted three times with 50 ml of benzene, each. The pooled benzene extracts are washed three times with 30 ml of water, dried over anhydrous sodium sulfate and evaporated from a water bath of 40° C. at a pressure of 20 to 25 millibar. The oily residue is dissolved in a mixture of 60 ml of benzene-tetrahydrofuran-8:2 and submitted to chromatography on a column prepared from 750 g of Kieselgel-60 in a solvent mixture of benzene-tetrahydrofuran. The fractionation is monitored by silicagel thin-layer chromatography in a developing solvent of ethyl acetate-pyridine-acetic acid-water-480:20:6:11, the $R_F$ value of the product is 0.70 to 0.76. The fractions containing the pure product are pooled and concentrated at a water bath of a temperature of 40° C. at 20 to 25 millibar to 100 ml. This residue is mixed with 500 ml of petroleum ether, the resulting suspension is filtered, washed twice with 100 ml of petroleum ether and dried in a vacuum exsiccator in the presence of sulfuric acid and paraffin shavings. Yield 45 g (65%).

$[\alpha]_D^{20} = +13.5°$ (c=1, tetrahydrofuran).

$R_F^2 = 0.70$ to 0.76.

Analysis calculated for $C_{37}H_{42}O_7N_6$ (682.75): Calculated: C 65.08, H 6.20, N 12.31 percent; Found: C 65.4, H 6.4, N 12.1 percent.

Step 2:
N-Benzyloxycarbonyl-N-methyl-D-phenylalanyl-L-prolyl-N$^\omega$-benzyloxycarbonyl-L-arginine-aldehyde 34.15 g (0.05 mole) of N-benzyloxycarbonyl-N-methyl-D-phenylalanyl-L-prolyl-N$^\omega$-benzyloxycarbonyl-L-arginine lactam (Example 1, Step 1) are dissolved in 150 ml of tetrahydrofuran, the solution is cooled to −20° C. and at constant stirring 0.0375 mole of lithium aluminum hydride, dissolved in tetrahydrofuran, is added. The progress of the reduction is monitored by thin-layer chromatography in a developing solvent system of ethyl acetate-pyridine-acetic acid-water-240:20:6:11 ($R_F$ value of lactam and aldehyde about 0.8 and 0.5, respectively). If required, further portions of lithium aluminum hydride are added, then the reaction mixture is acidified with N sulfuric acid to pH 2 under cooling and stirring. The solution is diluted with water (about 300 ml) until it turns opaque, then it is extracted twice with 100 ml of n-hexane. Afterwards the aqueous tetrahydrofuran layer is extracted twice with 250 ml of methylenechloride. The pooled methylenechloride extracts are washed twice with 50 ml of water, twice with 50 ml of 5 percent sodium hydrogen carbonate solution, then again twice with 50 ml of water, finally the solution is dried over anhydrous sodium sulfate and concentrated to 50 to 60 ml on a water bath of max. 40° C. at 20 to 25 millibar. Then 100 ml of benzene are added to the residue and concentration is repeated in a similar way. The concentrate is diluted with 100 ml of cyclohexane. The precipitate formed is filtered, washed twice with 30 ml of cyclohexane and dried in a vacuum desiccator over paraffin shavings. Yield 27 g (70%) containing one mole of cyclohexane according to analysis data.

$R_F^3 = 0.52$ to 0.62.

$[\alpha]_D^{20} = +16.8°$ (c=1, tetrahydrofurane).

Analysis calculated for $C_{37}H_{44}O_7N_6 \cdot C_6H_{12}$ (768.93): Calculated: C 67.16; H 7.34, N 10.93 percent; Found: C 66.6, H 7.2, N 10.4 percent.

Step 3:
N-Methyl-D-phenylalanyl-L-prolyl-L-arginine-aldehyde sulfate 23.1 g (0.03 mole) of N-benzyloxycarbonyl-N-methyl-D-phenylalanyl-L-prolyl-N$^\omega$-benzyloxycarbonyl-L-arginine-aldehyde (Example 1, Step 2) are dissolved in 150 ml of ethanol, 50 ml of deionized water and 48 ml of N sulfuric acid are added and the mixture is submitted to hydrogenolysis in the presence of 3 g of a 10 percent Pd/C catalyst. The progress of the hydrogenolysis is monitored by thin-layer chromatography in a developing solvent of ethyl acetate-pyridine-acetic acid-water-30:20:6:11 ($R_f$ values of the starting material, intermediary and final product about 0.9, 0.7 and 0.4, respectively). After completed reaction the catalyst is filtered and washed three times with 30 ml of deionized water. The filtrate and washings are combined and concentrated to about 100 ml in a rotary evaporator. The aqueous residue is diluted to about 200 ml with deionized water and its pH is controlled. If it is not between 6.0 and 6.5, it is adjusted with 0.1N sulfuric acid or an ion-exchange resin in OH cycle (i.e. AG 1X8), then the solution is freeze-dried. Yield 12.4 g (75%).

$R_F^6 = 0.39$ to 0.47

$[\alpha]_D^{20} = -131°$ (c=1, water).

Analysis calculated for $C_{21}H_{32}O_3N_6 \cdot 7/8(H_2SO_4) \cdot 2.5(H_2O)$ (547.37): Calculated: C 46.07, H 7.13, N 15.35, S 5.12 percent; Found: C 46.4, H 7.2, N 15.05, S 5.0 percent.

The starting materials can be prepared according to the following method:

N-Benzyloxycarbonyl-N-methyl-D-phenylalanyl-L-proline

Step A: Benzyloxycarbonyl-D-phenylalanine 2,4,5-trichlorophenyl ester 60.0 g (0.2 mole) of benzyloxycarbonyl-D-phenylalanine [H. Yajima and K. Kubo: J. Am. Chem. Soc. 87, 2039-2044 (1965)] and 39.4 g (0.2 mole) of 2,4,5-trichlorophenol are dissolved in 200 ml of tetrahydrofuran, the solution is cooled to 5° to 10° C., then at stirring 41.2 g (0.2 mole) of dicyclohexylcarbodiimide are added in about 30 minutes. The reaction mixture is stirred for 6 hours without refrigeration. The precipitated dicyclohexylurea is filtered, washed three times with 50 ml of tetrahydrofuran and the combined tetrahydrofurane solutions are evaporated at reduced pressure. The residue is crystallized from 300 ml of hot etanol, filtered, washed twice with 50 ml of ethanol having a temperature of 5° to 10° C., then the crystals are dried in a vacuum desiccator. Yield: 72 g (75%).

M. p.: 139°-141° C.

$[\alpha]_D^{20} = +37°$ (c=1, dimethylformamide)

Analysis calculated for $C_{23}H_{18}O_4NCl_3$ (478.75): Calculated: C 57.70, H 3.79, N 2.92, Cl 22.22 percent; Found: C 57.7, H 3.9, N 3.0, Cl 22.2 percent.

Step B: Benzyloxycarbonyl-D-phenylalanyl-L-proline 71.8 g (0.15 mole) of benzyloxycarbonyl-D-phenylalanine 2,4,5-trichlorophenyl ester (Example 1, Step A) are dissolved at stirring and at room temperature in 180 ml of anhydrous pyridine, then 17.3 g (0.15 mole) of L-proline and 21.0 ml (0.15 mole) of triethylamine are added. Stirring is continued till the dissolution of proline, then the reaction mixture is left to stand for 4 to 6 hours. Afterwards it is concentrated to 80 to 100 ml on a water bath having a temperature of 40° C. at 13 to 20 millibars and the residue is dissolved in a mixture of 250 ml of water and 90 ml of diethyl ether. The aqueous layer is washed twice with 30 ml of diethyl ether, the combined ether phases are washed twice with 30 ml of a 5 percent solution of sodium hydrogen carbonate, then the combined aqueous layers are acidified with 3N hydrochloric acid to pH 2. The separated oil is extracted three times with 120 ml of ethyl acetate, the combined ethyl acetate solutions are washed three times with 40 ml of water, dried over anhydrous sodium sulfate and subsequently concentrated to 50 to 100 ml on a water bath having a temperature of 40° C. at 15 to 20 millibars. The residue is crystallized from 200 ml of ether. The crystals are filtered, washed twice with 40 ml of ether. Yield 50.4 g (85%).

M.p.: 132° to 133° C.

$[\alpha]_D^{20} = -46.4°$ (c=2, dimethylformamide).

$R_F^3 = 0.5$.

Analysis calculated for $C_{22}H_{24}O_5N_2$ (396.43): Calculated: C 66.65, H 6.10, N 7.07 percent; Found: C 66.4, H 6.25, N 7.2 percent.

Step C:
N-Benzyloxycarbonyl-N-methyl-D-phenylalanyl-L-proline cyclohexylammonium salt 39.6 g (0.1 mole) of benzyloxycarbonyl-D-phenyl-alanyl-L-proline (Example 1, Step B) and 50 ml (0.8 mole) of methyliodide are dissolved in 300 ml of anhydrous tetrahydrofuran. To this soluton, cooled to 0° C., 13.2 g (0.3 mole) of sodium hydride suspension is added in 8 to 10 portions at constant stirring, and stirring is continued for two hours. Subsequently 500 ml of ethyl acetate are added to the reaction mixture to decompose the sodium hydroxide formed, then very cautiously 10 ml of water to decompose excess sodium hydride, finally the solution is evaporated from a water bath having a temperature of 40° C. at 15 to 20 millibars. The residue is dissolved in a mixture of 250 ml of water and 100 ml of diethyl ether. The aqueous layer is washed with 100 ml of diethyl ether and the combined diethyl ether phases with 50 ml of a 5 percent sodium hydrogen carbonate solution. The hydrogen carbonate and the aqueous layers are combined, acidified with potassium hydrogen sulfate to pH 2 and extracted twice with potassium hydrogen sulfate to pH 2 and extracted twice with 150 ml of ethyl acetate. The combined ethyl acetate phases are washed consecutively with 100 ml of water, 50 ml of a 10 percent solution of sodium thiosulfate and 100 ml of water, dried over anhydrous sodium sulfate and evaporated on a water bath having a temperature of max. 40° C. at 15 to 20 millibars. The residue is dissolved in 600 ml of benzene, 12 ml (0.105 mole) of cyclohexylamine are added and the solution is left to stand at room temperature. The crystals formed are filtered, washed twice with 200 ml of benzene and dried in a vacuum a desiccator over paraffin shavings. Yield 38.2 g (75%).

$R_F{}^3$=0.53–0.60 (and cyclohexylamine: 0.01–0.05).
M.p.: 160° to 163° C.
$[\alpha]_D{}^{20}$=+12.1° (c=1, methanol).

Analysis calculated for $C_{23}H_{26}O_5N_2 \cdot C_6H_{13}N$ (509.83): Calculated: C 68.34, H 7.71, N 8.25 percent; Found: C 68.5, H 7.8, N 8.3 percent.

$N^\alpha$-t-Butyloxycarbonyl-$N^\omega$-benzyloxycarbonyl-L-arginine lactam

Step D:
$N^\alpha$-t-Butyloxycarbonyl-$N^\omega$-benzyloxycarbonyl-L-arginine hydrate 65.8 g (0.2 mole) of t-butyloxycarbonyl-L-arginine hydrochloride hydrate [D. Yamashiro et al.: J. Am. Chem. Soc. 94, 2855–2859 (1972)] are dissolved in 100 ml of 4N sodium hydroxide, cooled to 5° to 10° C., then at constant stirring 80 ml (0.5 mole) of benzyloxycarbonyl chloride and about 150 ml of 4N sodium hydroxide are added at a rate assuring that the pH of the reaction mixture always exceeds 12. Afterwards the reaction mixture is stirred for further 3 to 4 hours, diluted with 150 ml of water and extracted with 100 ml of diethyl ether. The system separates into three phases. The lower two phases are repeatedly washed twice with 100 ml of diethyl ether, then 300 to 400 ml of methanol are added to get a homogeneous solution and the pH is adjusted, if necessary, with 4N sodium hydroxide to 12. After storing the solution for 6 to 8 hours it is extracted twice with 100 ml of a 1:1 mixture of petroleum ether-diethyl ether, the pH is adjusted to 6 to 7 with glacial acetic acid (about 50 ml required). Then the solution is extracted three times with 140 ml of methylenechloride, the methylenechloride solutions are pooled, washed twice with 60 ml of water and evaporated from a water bath having a temperature of 40° C. at 25 to 30 millibars. 300 ml of benzene and 600 ml of water are added to the residue which is stirred for 2 to 3 hours at 20° C., then left to stand at 10° C. overnight. The crystals formed are filtered, washed with 300 ml of water and 300 ml of benzene and dried in a vacuum desiccator in the presence of phosphorus pentoxide and paraffin shavings. Yield 60 g (70%).

M.p.: 122° to 124° C.
$[\alpha]_D{}^{20}$=−20.7° (c=1, pyridine).

Analysis calculated for $C_{19}H_{28}O_6N_4 \cdot H_2O$ (426.46): Calculated: C 53.51, H 7.09, N 13.14 percent; Found: C 53.35, H 7.2, N 13.1 percent.

Step E:
$N^\alpha$-t-Butyloxycarbonyl-$N^\omega$-benzyloxycarbonyl-L-arginine lactam 59.7 g (0.14 mole) of $N^\alpha$-butyloxycarbonyl-$N^\omega$-benzyloxycarbonyl-arginine hydrate (Example 1, Step D) and 19.6 g (0.14 mole) of triethylamine are dissolved in 200 ml of tetrahydrofuran. The solution is cooled to −10° C., and at this temperature and at stirring 18.5 ml (0.14 mole) of isobutyloxycarbonyl chloride are added, then after 10 minutes 19.6 ml (0.14 mole) of triethylamine. Stirring is continued for an other hour at 0° C. and an hour without refrigeration, then the mixture is poured over 1000 ml of ice-water. The crystals formed are filtered, washed twice with 100 ml of ice-water, then they are dissolved in 280 ml of chloroform. The chloroform solution is washed twice with 100 ml of ice-water, dried over anhydrous calcium chloride and evaporated on a water bath having a temperature of max. 40° C. at 20 to 25 millibars. The crystalline residue is suspended in 70 ml of petroleum ether, filtered, washed twice with 30 ml of petroleum ether, and dried in a vacuum desiccator in the presence of phosphorus pentoxide. Yield 44 g (81%).

M.p.: 164° to 166° C.
$[\alpha]_D{}^{20}$=−24° (c=1, tetrahydrofuran).

Analysis calculated for $C_{19}H_{26}O_5N_4$ (390.43): Calculated: C 58.44, H 6.71, N 14.35 percent; Found: C 58.7, H 6.8, N 14.1 percent.

EXAMPLE 2

N,N-Dimethyl-D-phenylalanyl-L-prolyl-L-arginine-aldehyde sulfate

Step 1:
N,N-Dimethyl-D-phenylalanyl-L-prolyl-$N^\omega$-benzyloxycarbonyl-L-arginine lactam hydrochloride 4.3 g (0.011 mole) of $N^\alpha$-t-butyloxycarbonyl-$N^\omega$-benzyloxycarbonyl-L-arginine lactam (Example 1, Step E) are transformed according to the procedure described in Example 1, Step 1, by using proportional amounts of solvents and reagents. The resulting suspension is added to the following mixed anhydride.

3.26 g (0.01 mole) of N,N-dimethyl-D-phenylalanyl-L-proline hydrate and 2.2 ml (0.02 mole) of N-methylmorpholine are dissolved in a mixture of 50 ml of benzene and 5 ml of ethanol. The mixture is concentrated to 10 to 15 ml on a water bath having a temperature of max. 40° C. at 40 to 50 millibars, subsequently four times 40 ml portions of benzene are distilled off the mixture which is finally evaporated to dryness. The residue is dissolved in 10 ml of dimethylformamide, cooled to −15° C., at this temperature 1.32 ml (0.01 mole) of isobutyloxycarbonyl chloride and after 5 minutes the above suspension in dimethylformamide are added. The reaction mixture is stirred for one hour at −15° C. and for an other hour at 0° C., then 40 ml of ethyl acetate are added and the precipitated salts are filtered. 20 ml of water are poured into the filtrate and the layers formed are separated. The aqueous dimethylformamide layer is extracted three times with 5 ml of ethyl acetate. The combined ethyl acetate solutions are washed twice with 15 ml of water, twice with 15 ml of a 5% solution of sodium hydrogen carbonate, then again twice with 15 ml of water, the extract is dried over anhydrous sodium sulfate and concentrated to 10 to 15 ml on a water bath having a temperature of 40° C. at 20 to 25 millibars. Then hydrochloric acid-ethyl acetate is added to the residual solution, ensuring that the gaseous phase should be acidic, and the solution is diluted with 30 to 40 ml of diethyl ether. The precipitate formed is filtered, washed with diethyl ether and dried in the presence of sulfuric acid and potassium hydroxide in a vacuum desiccator. Yield 2.7 g (45%).

$R_f{}^4$=0.43.
$[\alpha]_D{}^{20}$=−56.0° (c=1 chloroform).

Analysis calculated for $C_{30}H_{38}O_5N_6 \cdot 9/5HCl \cdot 2H_2O$ (666.13): Calculated: C 54.09, H 6.90, N 12.62, Cl 9.58 percent; Found: C 54.0, H 7.0, N 12.6, Cl 9.8 percent.

Step 2:
N,N-Dimethyl-D-phenylalanyl-L-prolyl-$N^\omega$-benzyloxycarbonyl-L-arginine-aldehyde sulfate 2.4 g (0.004 mole) of N,N-dimethyl-D-phenylalanyl-L-prolyl-$N^\omega$-benzyloxycarbonyl-L-arginine lactam hydrochloride (Example 2, Step 1) are dissolved in 15 ml of tetrahydrofurane, cooled to −20° C. and at constant stirring 0.003 mole of a lithium aluminum hydride suspension in tetrahydrofuran is added. The progress of the reduction is monitored by thin-layer chromatography in a developing system of ethyl acetate-pyridine-acetic acid-water-60:20:6:11 ($R_F$ value of the lactam and of the aldehyde being about 0.35 and 0.2, respectively). If required, further portions of lithium aluminum hydride are added, then the reaction mixture is acidified to pH 5 with N-sulfuric acid at cooling and stirring (about 30 ml) and it is extracted twice with 15 ml of chloroform. The aqueous tetrahydrofuran layer is extracted three times with 20 ml of n-butanol. The combined butanol extracts are washed with 10 ml of water saturated with n-butanol and the solution is concentrated to 5 to 10 ml on a water bath having a temperature of max. 40° C. at 15 to 20 millibars. The residue is diluted with 30 ml of ether, the precipitate formed is filtered, washed twice with 10 ml of diethyl ether and twice with 10 ml of petroleum ether, then it is dissolved in a mixture of 20 ml of chloroform and 5 ml of methanol. The insoluble residue is filtered, and the filtrate is evaporated according to the above method.

The oily residue is mixed with 30 ml of diethyl ether, the precipitate formed is filtered, washed twice with 20 ml of diethyl ether and twice with 20 ml of petroleum ether, then it is dried in a vacuum desiccator in the presence of paraffin shavings, sulfuric acid and potassium hydroxide. Yield 2.25 g (85%).

$R_F{}^5 = 0.48$ to 0.54.

Analysis calculated for $C_{30}H_{38}O_5N_6 \cdot H_2SO_4$ (660.73): Calculated: C 54.53, H 6.10, N 12.72, S 4.84 percent; Found: C 55.0, H 6.5, N 12.1, S 4.7 percent.

Step 3:
N,N-Dimethyl-D-phenylalanyl-L-prolyl-L-arginine-aldehyde sulfate 1.32 g (0.002 mole) of N,N-dimethyl-D-phenylalanyl-L-prolyl-N$^\omega$-benzyloxycarbonyl-L-arginine-aldehyde sulfate (Example 2, Step 2) is dissolved in a mixture of 5 ml of deionized water and 15 ml of ethanol and hydrogenated in the presence of 0.2 g of 10% Pd/C catalyst. The catalyst is filtered, and washed twice with 10 ml of deionized water. The combined filtrate and washings are concentrated to 5 to 10 ml on a water bath having a temperature of max. 40° C. at 15 to 20 millibars, then the solution is diluted to 20 ml with deionized water. If necessary, the pH is adjusted either with 0.1N sulfuric acid or with an ion exchange resin (e.g. AG 1X8) in OH$^-$ cycle to 6.0 to 6.5, then the solution is freeze-dried. Yield 0.85 g (80%).

$R_F{}^6 = 0.35$ to 0.39.

Analysis calculated for $C_{22}H_{34}O_3N_6 \cdot H_2SO_4 \cdot 3(H_2O)$ (566.67): Calculated: C 46.60, H 7.47, N 14.82, S 5.66 percent; Found: C 45.5, H 7.4, N 14.3, S 5.2 percent.

The starting material N,N-dimethyl-D-phenylalanyl-L-proline hydrate can be prepared according to the following method:

11.9 g (0.03 mole) of benzyloxycarbonyl-D-phenylalanyl-L-proline (Example 1, Step B) are dissolved in 200 ml of 50 percent aqueous methanol and hydrogenated in the presence of 9.7 ml (about 0.12 mole) of formaldehyde solution and 6 g of 10 percent Pd/C catalyst. The progress of the reaction is monitored by thin-layer chromatography in a developing solvent of ethyl acetate-pyridine-acetic acid-water-30:20:6:11 (the $R_F$ value of the starting material and the end product being 0.95 and 0.45, respectively). After completed reaction the catalyst is filtered, washed twice with 50 ml of aqueous methanol and the combined filtrate and washings are evaporated on a water bath having a temperature of 40° C. at 20 to 25 millibars. The residue is dissolved in 60 ml of ethyl acetate, 0.5 ml of water is added and the solution is left at 5° to 10° C. overnight. The crystals formed are filtered, washed twice with 15 ml of ethyl acetate having a temperature of 5° to 10° C., and dried in a vacuum desiccator over paraffin shavings, sulfuric acid and potassium hydroxide. Yield 6.5 g (67%).

M.p.: 228° to 229° C.

$[\alpha]_D{}^{20} = -159°$ (c=1, water).

Analysis calculated for $C_{16}H_{22}O_3N_2 \cdot H_2O$ (308.37): Calculated: C 62.31, H 7.85, N 9.08 percent; Found: C 62.5, H 8.0, N 8.95 percent.

EXAMPLE 3

N-Ethyl-D-phenylalanyl-L-prolyl-L-arginine-aldehyde sulfate

Step 1:
N-Benzyloxycarbonyl-N-ethyl-D-phenylalanyl-L-prolyl-N$^\omega$-benzyloxycarbonyl-L-arginine lactam 2.1 g (0.005 mole) of N-benzyloxycarbonyl-N-ethyl-D-phenylalanyl-L-proline and 2.15 g (0.0055 mole) of N$^\alpha$-t-butyloxycarbonyl-N$^\omega$-benzyloxycarbonyl-L-arginine lactam (Example 1, Step E) are transformed and condensed, respectively, according to the procedure described in Example 1, Step 1, by using proportional amounts of reagents and solvents. However, during the processing of the reaction mixture and during column chromatography the product content is monitored by thin-layer chromatography in a developing system of benzene-tetrahydrofurane-8:2. The fractions containing the pure main product ($R_F = 0.4$ to 0.5) are combined and evaporated on a water bath having a temperature of 40° C. at 15 to 20 millibars. The residue is worked up with diisopropyl ether, filtered, washed with diisopropyl ether and dried in a vacuum exsiccator in the presence of sulfuric acid and paraffin shavings. Yield 1.9 g (54%).

$R_F{}^2 = 0.75$ to 0.85.

Step 2:
N-Benzyloxycarbonyl-N-ethyl-D-phenylalanyl-L-prolyl-N$^\omega$-benzyloxycarbonyl-L-arginin-aldehyde 1.4 g (0.002 mole) of N-benzyloxycarbonyl-N-ethyl-D-phenylalanyl-L-prolyl-N$^\omega$-benzyloxycarbonyl-L-arginine lactam (Example 3, Step 1) is transformed according to the procedure described in Example 1, Step 2, by using proportional amounts of reagents and solvents. Yield 1.15 g (72%) which contains according to the analysis one mole of cyclohexane.

$R_F{}^3 = 0.55$ to 0.65.

Analysis calculated for $C_{38}H_{46}O_7N_6 \cdot C_6H_{12}$ (782.95): Calculated: C 67.49, H 7.47, N 10.73 percent; Found: C 67.6, H$_{7.5}$, N 10.5 percent.

Step 3:
N-Ethyl-D-phenylalanyl-L-prolyl-L-arginine-aldehyde sulfate 0.78 g (0.001 mole) of N-benzyloxycarbonyl-N-ethyl-D-phenylalanyl-L-prolyl-N$^\omega$-benzyloxycarbonyl-L-arginine-aldehyde (Example 3, Step 2) is transformed according to the procedure described in Example 1, Step 3, by applying proportional amounts of reagents and solvents. Yield 0.75 g (70%).

$R_F{}^6 = 0.4$ to 0.5.

Analysis calculated for C$_{22}$H$_{34}$O$_3$N$_6$.5/6(H$_2$SO$_4$).3.5(H$_2$O) (575.27): Calculated: C 45.93, H 7.48, N 14.61, S 4.64 percent; Found: C 46.1, H 7.6, N 14.2, S 4.6 percent.

The starting material N-benzyloxycarbonyl-N-ethyl-D-phenyl-alanine-L-proline can be prepared as follows:

Step A: N-Ethyl-D-phenylalanine 8.28 g (0.05 mole) of D-phenylalanine are dissolved in 100 ml of 20 percent aqueous ethanol and hydrogenated in the presence of 5.65 ml (0.1 mole) of acetaldehyde and 2 g of 10 percent Pd/C catalyst for two days. The catalyst is filtered, washed with 60 ml of 2N hydrochloric acid and the pH of the combined aqueous solutions is adjusted with 4N sodium hydroxide to 7. The precipitate formed is filtered, washed three times with 20 ml of water and dried in a vacuum desiccator over anhydrous calcium chloride. Yield 4.85 g (50%).

$[\alpha]_D^{20} = -53°$ (c=1, 0.1N sodium hydroxide).

Analysis calculated for C$_{11}$H$_{15}$O$_2$N (193.24): Calculated: C 68.37, H 7.82, N 7.25 percent; Found: C 68.5, H 7.65, N 7.2 percent.

Step B: N-Benzyloxycarbonyl-N-ethyl-D-phenylalanine 2.9 g (0.015 mole) of N-ethyl-D-phenylalanine (Example 3, Step A) are dissolved in 22.5 ml of 2N sodium hydroxide, 10 ml of dioxane are added, the mixture is cooled to 5° to 10° C., then 2.5 ml (about 0.017 mole) of benzyloxycarbonyl chloride are added and the reaction mixture is stirred for 3 hours at cooling. Subsequently it is diluted with 40 ml of water and extracted with 30 ml of a mixture of diethyl ether-petroleum ether-1:1, when a three-phase system is formed. The two lower phases are again extracted with 30 ml of diethyl ether, then the combined diethyl ether layers are washed with 20 ml of water. The aqueous layers are combined and acidified with N sulfuric acid to pH 2. The separated product is extracted three times with 30 ml of ethyl acetate. The ethyl acetate layers are combined, washed twice with 20 ml of water, dried over anhydrous sodium sulfate and evaporated on a water bath having a temperature of max. 40° C. at 15 to 20 millibars. Yield 2.7 g (55%) of an oil.

$R_F^2 = 0.5$ to 0.6.

Step C: N-Benzyloxycarbonyl-N-ethyl-D-phenylalanyl-L-proline 2.6 g (0.008 mole) of N-benzyloxycarbonyl-N-ethyl-D-phenylalanine (Example 3, Step 2) are dissolved in 10 ml of tetrahydrofuran and at 0° C. 1.6 g (0.008 mole) of 2,4,5-trichlorophenol and 1.65 g (0.008 mole) of dicyclohexylcarbodiimide are added, then the mixture is left to stand at room temperature for 4 hours. The residue is dissolved in 40 ml of benzene, washed twice with 20 ml of a 5 percent solution of sodium hydrogen carbonate, twice with 20 ml of water, then it is dried over anhydrous sodium sulfate and evaporated on a water bath having a temperature of about 40° C. at 15 to 20 millibars. The residual oil is dissolved in 10 ml of pyridine, 0.92 g (0.008 mole) of L-proline and 1.12 ml (0.008 mole) of triethylamine are added and the mixture is stirred till the dissolution of proline at room temperature. Then the solution is left to stand for 4 to 5 hours, subsequently it is evaporated on a water bath having a temperature of about 40° C. at 15 to 20 millibars. The residue is dissolved in a mixture of 25 ml of water and 10 ml of diethyl ether. The aqueous layer is washed twice with 10 ml of diethyl ether and the combined ether extracts are washed with 10 ml of a 5 percent solution of sodium hydrogen carbonate. The aqueous layers are combined and acidified to pH 2 with 3N hydrochloric acid. The separated product is extracted three times with 15 ml of benzene, the benzene layers are combined, washed three times with 5 ml of water, dried over anhydrous sodium sulfate and evaporated on a water bath having a temperature of about 40° C. at 15 to 20 millibars. Yield 2.2 g (64%) of an oil.

$R_F^5 = 0.5$ to 0.6.

EXAMPLE 4

N-Isobutyl-D-phenylalanyl-L-prolyl-L-arginine-aldehyde sulfate

Step 1: N-Benzyloxycarbonyl-N-isobutyl-D-phenylalanyl-L-prolyl-N$^\omega$-benzyloxycarbonyl-L-arginine lactam 2.26 g (0.005 mole) of N-benzyloxycarbonyl-N-isobutyl-D-phenylalanyl-L-proline and 2.15 g (0.0055 mole) of N$^\alpha$-t-butyloxycarbonyl-N$^\omega$-benzyloxycarbonyl-L-arginine lactam (Example 1, Step E) are transformed and condensed, respectively, according to the procedure described in Example 1, Step 1, by applying proportional amounts of reagents and solvents. During the processing of the reaction mixture and during the column chromatography the product content of the fractions is monitored by thin-layer chromatography in a developing solvent system of ethyl acetate-pyridine-acetic acid-water-480:20:6:11. The fractions containing the pure product ($R_F^2=0.75$ to 0.85) are pooled, evaporated on a water bath having a temperature of about 40° C. at 15 to 20 millibars, the residue is processed with petroleum ether, filtered, washed with petroleum ether and dried in a vacuum desiccator over paraffin shavings. Yield: 2.7 g (75%)

$R_F^2 = 0.75$ to 0.85.

$[\alpha]_D^{20} = -5.8°$ (c=1, tetrahydrofurane).

Analysis calculated for C$_{40}$H$_{48}$O$_7$N$_6$.$\frac{2}{3}$(C$_4$H$_8$O) (772.90): Calculated: C 66.30, H 6.95, N 10.87 percent; Found: C 65.0, H 6.8, N 10.80 percent.

Step 2: N-Benzyloxycarbonyl-N-isobutyl-D-phenylalanyl-L-prolyl-N$^\omega$-benzyloxycarbonyl-L-arginine-aldehyde 1.45 g (0.002 mole) of N-benzyloxycarbonyl-N-isobutyl-D-phenylalanyl-L-prolyl-N$^\omega$-benzyloxycarbonyl-L-arginine lactam (Example 4, Step 1) are reduced according to the procedure described in Example 1, Step 2 by using proportional amounts of reagents and solvents. Yield 1.0 g (62.%)

$R_F^3 = 0.24$.

$[\alpha]_D^{20} = +2.3$ (c=1, tetrahydrofurane).

Analysis calculated for C$_{40}$H$_{50}$O$_7$N$_6$.$\frac{1}{4}$(C$_6$H$_{12}$) (747.89): Calculated: C 66.64, H 7.14, N 11.24 percent; Found: C 66.3, H 7.1, N 11.2 percent.

Step 3: N-Isobutyl-D-phenylalanyl-L-prolyl-L-arginine-aldehyde sulfate 0.81 g (0.001 mole) of N-benzyloxycarbonyl-N-isobutyl-D-phenylalanyl-L-propyl-N$^\omega$-benzyloxycarbonyl-L-arginine-aldehyde (Example 4, Step 2) is transformed according to the procedure described in Example 1, Step 3 by using proportional amounts of reagents and solvents. Yield 0.45 g (80%)

$R_F^6=0.64$.

Analysis calculated for $C_{24}H_{38}O_3N_6.H_2SO_4.4(H_2O)$ (628.74): Calculated: C 45.84, H 7.69, N 13.36, S 5.1 percent; Found: C 45.8, H 7.2, N 13.4, S 4.9 percent.

The starting material N-benzyloxycarbonyl-N-isobutyl-D-phenylalanyl-L-proline can be prepared as follows:

Step A: N-Isobutyl-D-phenylalanine

Starting from 8.25 g (0.05 mole) of D-phenylalanine, and using the procedure described in Example 3, Step A, except that 9.1 ml (0.1 mole) of isobutyraldehyde are used instead of acetaldehyde, 8.7 g (70%) of the product are obtained.

$[\alpha]_D^{20}=-29.9°$ (c=1, in 0.1N sodium hydroxide).

Analysis calculated for $C_{13}H_{19}O_2N.\frac{1}{2}(H_2O)$ (230.30): Calculated: C 67.79, H 8.75, N 6.08 percent; Found: C 67.2, H 8.9, N 6.15 percent.

Step B: N-Benzyloxycarbonyl-N-isobutyl-D-phenylalanine 3.32 g (0.015 mole) of N-isobutyl-D-phenylalanine (Example 4, Step A) are transformed according to the procedure described in Example 3, Step B. Yield 3.2 g (60%) of an oil.

$R_F^4=0.6$ to 0.7.

Step C: N-Benzyloxycarbonyl-N-isobutyl-D-phenylalanyl-L-proline 2.85 g (0.008 mole) of N-benzyloxycarbonyl-N-isobutyl-D-phenylalanine (Example 4, Step B) are transformed according to the procedure described in Example 3, Step C. Yield 2.45 g (67%) of an oil.

$R_F^5=0.65$ to 0.70.

EXAMPLE 5

N-Methyl-D-alloisoleucyl-L-prolyl-L-arginine-aldehyde sulfate

Step 1: N-Benzyloxycarbonyl-N-methyl-D-alloisoleucyl-L-prolyl-Nω-benzyloxycarbonyl-L-arginine lactam 4.3 g (0.011 mole) of $N^\alpha$-t-butyloxycarbonyl-$N^\omega$-benzyloxycarbonyl-L-arginine lactam (Example 1, Step E) and 4.8 g (0.01 mole) of N-benzyloxycarbonyl-N-methyl-D-alloisoleucyl-L-proline cyclohexyl-ammonium salt are transformed according to the procedure described in Example 1, Step 1, by using proportional amounts of reagents and solvents. During column chromatography the fractions containing the product migrating with $R_F^2=0.74$ to 0.80 are pooled, evaporated, the residue obtained is processed with 40 ml of diisopropyl ether, the precipitate is filtered, washed twice with 20 ml of diisopropyl ether and dried in a vacuum desiccator over sulfuric acid and paraffin shavings. Yield 4.3 g (66%).

$R_F^2=0.74$ to 0.80.

Analysis calculated for $C_{34}H_{44}O_7N_6$ (648.74): Calculated: C 62.94, H 6.84, N 12.96 percent; Found: C 63.1, H 6.9, N 12.7 percent.

Step 2: N-Benzyloxycarbonyl-N-methyl-D-alloisoleucyl-L-prolyl-Nω-benzyloxycarbonyl-L-arginine-aldehyde 3.25 g (0.005 mole) of N-benzyloxycarbonyl-N-methyl-D-alloisoleucyl-L-prolyl-Nω-benzyloxycarbonyl-L-arginine lactam (Example 5, Step 1) are transformed according to the procedure described in Example 1, Step 2, by using proportional amounts of reagents and solvents. Yield 2.5 g (66%) of a product containing according to elementary analysis one mole of cyclohexane.

$R_F^3=0.55$.

Analysis calculated for $C_{34}H_{46}O_7N_6.C_6H_{12}$ (734.91): Calculated: C 65.37, H 7.95, N 11.43 percent; Found: C 65.0, H 7.8, N 11.6 percent.

Step 3: N-Methyl-D-alloisoleucyl-L-prolyl-L-arginine-aldehyde sulfate 1.47 g (0.002 mole) of N-benzyloxycarbonyl-N-methyl-D-alloisoleucyl-L-prolyl-Nω-benzyloxycarbonyl-L-argininealdehyde (Example 5, Step 2) are transformed according to the procedure described in Example 1, Step 3, by using proportional amounts of reagents and solvents. Yield 0.85 g (87%).

$R_F^6=0.4$.

Analysis calculated for $C_{18}H_{34}O_3N_6.H_2SO_4.4(H_2O)$ (552.65): Calculated: C 39.12, H 8.02, N 15.21, S 5.80 percent; Found: C 39.2, H 7.70, N 15.1, S 5.7 percent.

The starting material N-benzyloxycarbonyl-N-methyl-D-alloisoleucyl-L-proline cyclohexalammonium salt can be prepared according to the following method:

Step A: N-Benzyloxycarbonyl-D-alloisoleucyl-L-proline cyclohexylammonium salt 13.3 g (0.05 mole) of benzyloxycarbonyl-D-alloisoleucine [M. Winitz et al: J. Am. Chem. Soc. 98, 2423–2430 (1956)] and 9.9 g (0.05 mole) of 2,4,5-trichlorophenol are dissolved in 50 ml of ethyl acetate, 10.2 g (0.05 mole) of dicyclohexylcarbodiimide are added and the mixture is left to stand overnight. The precipitated dicyclohexylurea is filtered, and the filtrate is evaporated on a water bath having a temperature of about 40° C. at 15 to 20 millibars. The residue is dissolved in 100 ml of n-hexane, extracted with 20 ml of 1N sodium hydroxide and twice with 20 ml of water, then the extract is dried over anhydrous sodium sulfate and evaporated according to the method described above. The residue is dissolved in 50 ml of pyridine, 5.7 g (0.05 mole) of L-proline and 7.0 ml (0.05 mole) of triethylamine are added, the mixture is stirred till the dissolution of L-proline and is left to stand overnight. Then the mixture is evaporated on a water bath having a temperature of about 40° C. at 15 to 20 millibars. The residue is dissolved in 50 ml of a 5 percent sodium hydrogen carbonate solution and 50 ml of diethyl ether. The aqueous layer is washed twice with 30 ml of ether, then it is acidified with 3N hydrochloric acid to pH 3. The separated product is extracted three times with 30 ml of ethyl acetate, the ethyl acetate extracts are combined, washed three times with 30 ml of water, dried over anhydrous sodium sulfate and evaporated according to the method described above. The residue is dissolved in 100 ml of diisopropyl ether, 6.0 ml (0.052 mole) of cyclohexylamine are added and the solution is left to stand for 4 to 5 hours. The crystals formed are filtered, washed three times with 30 ml of diisopropyl ether and dried in a vacuum desiccator over sulfuric acid and potassium hydroxide. Yield 14.5 g (6.2%).

M.p.: 138° to 140° C.

$R_F^3=0.35$ to 0.40.

$[\alpha]_D^{20}=-30.7°$ (c=1, methanol).

Analysis calculated for $C_{19}H_{26}O_5N_2 \cdot C_6H_{13}N$ (461.59): Calculated: C 65.05, H 8.52, N 9.10 percent; Found: C 65.4, H 8.5, N 9.05 percent.

Step B:
N-Benzyloxycarbonyl-N-methyl-D-alloisoleucyl-L-proline cyclohexylammonium salt 9.25 g (0.02 mole) of benzyloxycarbonyl-D-alloisoleucyl-L-proline cyclohexylammonium salt (Example 5, Step A) are dissolved in 50 ml of diethylether and 50 ml of 0.5N sulfuric acid. The aqueous layer is extracted with 20 ml of diethylether and the combined ether layers are washed three times with 30 ml of water, then the extract is dried over anhydrous sodium sulfate and evaporated on a water bath having a temperature of about 40° C. at 20 to 30 millibars. The evaporation residue, N-benzyloxycarbonyl-D-alloisoleucyl-L-proline, is transformed according to the procedure described in Example 1, Step 3 by using proportional amounts of reagents and solvents. Yield 8.1 g (85%).

M.p.: 120° to 123° C.
$R_F^3 = 0.55$ to 0.60.
$[\alpha]_D^{20} = +43.8°$ (c=1, methanol).

Analysis calculated for $C_{20}H_{28}O_5N_2 \cdot C_6H_{13}N$ (475.61): Calculated: C 65.65, H 8.69, N 8.83 percent; Found: C 65.6, H 8.7, N 8.75 percent.

EXAMPLE 6

N-n-Hexyl-D-phenylalanyl-L-prolyl-L-arginine-aldehyde sulfate

Step 1:
N-Benzyloxycarbonyl-N-n-hexyl-D-phenylalanyl-L-prolyl-$N^\omega$-benzyloxycarbonyl-L-arginine-aldehyde 3.5 g (0.01 mole) of N-n-hexyl-D-phenylalanyl-L-proline (Step A) are dissolved in a mixture of 10 ml of dioxane and 14 ml of 2N sodium hydroxide, then 2.1 ml (0.028 mole) of benzyloxycarbonyl chloride are added at 5° to 10° C. and the mixture is stirred for 4 hours. Subsequently the reaction mixture is diluted with 30 ml of water and extracted twice with 20 ml of petroleum ether. The aqueous layer is acidified with 1N sulfuric acid to pH 2 to 3 and extracted three times with 20 ml of ethyl acetate. The combined ethyl acetate layers are washed three times with 10 ml of water, dried over anhydrous sodium sulfate and evaporated at a pressure of 20 to 25 millibars. Yield 2.9 g (60%) oil.

$R_F^2 = 0.48$.

This product and 2.58 g (0.0066 mole) of $N^\alpha$-t-butyloxycarbonyl-$N^\omega$-benzyloxycarbonyl-L-arginine lactam (Example 1, Step E) are transformed according to the procedure described in Example 1, Step 1 by using proportional amounts of reagents and solvents. After column chromatography the fractions containing the pure main product ($R_F^2 = 0.68$) are pooled and evaporated to 20 to 35 millibars. Yield 2.7 g (60%) of an oily product.

$R_F^2 = 0.68$.

This product is transformed according to the procedure described in Example 1, Step 2, by using proportional amounts of reagents and solvents. Yield 2.2 g (80%).

$R_F^2 = 0.53$.

Analysis calculated for $C_{42}H_{54}O_7N_6$ (699.82): Calculated: C 66.82, H 7.21, N 11.13 percent; Found: C 66.5, H 7.4, N 11.4 percent.

Step 2:
N-n-Hexyl-D-phenylalanyl-L-prolyl-L-arginine-aldehyde sulfate 0.74 g (0.001 mole) of N-benzyloxycarbonyl-N-n-hexyl-D-phenylalanyl-L-prolyl-$N^\omega$-benzyloxycarbonyl-L-arginine-aldehyde (Example 6, Step 1) is transformed according to the procedure described in Example 1, Step 3, by using proportional amounts of reagents and solvents.

$R_F^6 = 0.75$.

Analysis calculated for $C_{26}H_{42}O_3N_6 \cdot H_2SO_4 \cdot 4(H_2O)$ (656.79): Calculated: C 47.54, H 7.98, N 12.80, S 4.88 percent; Found: C 47.6, H 8.1, N 12.7, S 4.8 percent.

The starting material N-n-hexyl-D-phenylalanyl-L-proline can be prepared according to the following method:

7.9 g (0.02 mole) of N-benzyloxycarbonyl-D-phenylalanyl-L-proline (Example 1, Step B) and 4.9 ml (0.04 mole) of caprylaldehyde are dissolved in 100 ml of 80 percent ethanol and the solution is submitted to hydrogenolysis in the presence of 6 g of 10 percent Pd/C catalyst. By the end of the reaction the catalyst is filtered and the filtrate is evaporated. The crystalline residue is suspended in 20 ml of water, filtered and washed twice with water, then it is dried over phosphorus pentoxide in a vacuum desiccator. Yield 3.0 g (60%).

$R_F^5 = 0.6$.
$[\alpha]_D^{20} = -97.3°$ (c=1, 0.1N sodium hydroxide).

Analysis calculated for $C_{20}H_{30}O_3N_2$ (346.45): Calculated: C 69.33, H 8.73, N 8.08 percent; Found: C 68.9, H 8.8, N 8.0 percent.

EXAMPLE 7

N-Methyl-D-phenylalanyl-L-prolyl-D-arginine-aldehyde sulfate

Step 1:
N-Benzyloxycarbonyl-N-methyl-D-phenylalanyl-L-prolyl-$N^\omega$-benzyloxycarbonyl-D-arginine lactam 4.3 g (0.011 mole) of $N^\alpha$-t-butyloxycarbonyl-$N^\omega$-benzyloxycarbonyl-D-arginine lactam and 5.09 g (0.01 mole) of N-benzyloxycarbonyl-N-metyl-D-phenylalanyl-L-proline cyclohexylammonium salt (Example 1, Step C) are transformed and condensed according to the procedure described in Example 1, Step 1, by using proportional amounts of reagents and solvents. Yield 4.5 g (65%).

$[\alpha]_D^{20} = +28.3°$ (c=1, tetrahydrofuran).
$R_F = 0.55-0.65$ (ethylacetate), $R_F = 0.7-0.8$ (D,L,L form).

Analysis calculated for $C_{37}H_{42}O_7N_6$ (682.75): Calculated: C 65.08, H 6.20, N 12.31 percent; Found: C 65.2, H 6.3, N 12.2 percent.

Step 2:
N-Benzyloxycarbonyl-N-methyl-D-phenylalanyl-L-prolyl-$N^\omega$-benzyloxycarbonyl-D-arginine-aldehyde 3.41 g (0.005 mole) of N-benzyloxycarbonyl-N-methyl-D-phenylalanyl-L-prolyl-$N^\omega$-benzyloxycarbonyl carbonyl-D-arginine lactam (Example 7, Step 1) are reduced according to the procedure described in Example 1, Step 2 by using proportional amounts of reagents and solvents. Yield: 2.7 g (70%) of a product containing according to the elementary analysis one mole of cyclohexane.

$R_F^3 = 0.57-0.67$.

$[\alpha]_D^{20} = +45.5°$ (c=1, tetrahydrofuran).

Analysis calculated for $C_{37}H_{44}O_7N_6 \cdot C_6H_{12}$ (768.93):
Calculated: C 67.16, H 7.34, N 10.93 percent; Found: C 66.8, H 7.1, N 10.8 percent.

Step 3:
N-Methyl-D-phenylalanyl-L-prolyl-D-arginine-aldehyde sulfate 2.31 g (0.003 mole) of N-benzyloxycarbonyl-N-methyl-D-phenylalanyl-L-prolyl-$N^\omega$-benzyloxycarbonyl-D-arginine-aldehyde (Example 7, Step 2) are submitted to hydrogenolysis according to the procedure described in Example 1, Step 3 by using proportional amounts of reagents and solvents. Yield 1.24 g (75%).

$R_F^6 = 0.39–0.47$.

$[\alpha]_D^{20} = -75°$ (c=1, water).

The starting material, $N^\alpha$-t-butyloxycarbonyl-$N^\omega$-benzyloxycarbonyl-D-arginine lactam can be prepared according to the following method:

5.97 g (0.014 mole) of $N^\alpha$-t-butyloxycarbonyl-$N^\omega$-benzyloxycarbonyl-D-arginine hydrate, prepared according to the procedure described in Example 1, Step D, except that t-butyloxycarbonyl-D-arginine hydrochloride hydrate is used as starting material, is transformed according to the method used in Example 1, Step E, by using proportional amounts of reagents and solvents. Yield 40 g (73%).

M.p.: 155° to 156° C.

$[\alpha]_D^{20} = +24°$ (c=1, tetrahydrofurane).

EXAMPLE 8

N-Methyl-D-phenylalanyl-L-prolyl-DL-arginine-aldehyde sulfate

Step 1:
N-Benzyloxycarbonyl-N-methyl-D-phenylalanyl-L-prolyl-$N^\omega$-benzyloxycarbonyl-DL-arginine lactam 4.3 g (0.011 mole) of $N^\alpha$-t-butyloxycarbonyl-$N^\omega$-benzyloxycarbonyl-DL-arginine lactam and 5.09 g (0.010 mole) of N-benzyloxycarbonyl-N-methyl-D-phenylalanyl-L-proline cyclohexylammonium salt (Example 1, Step C) are transformed according to the procedure described in Example 1, Step 1, by using proportional amounts of reagents and solvents. Yield 4.0 g (60%).

$[\alpha]_D^{20} = +21°$ (c=1, tetrahydrofuran).

$R_F = 0.55–0.65$ (D,L,D form) and $R_F = 0.7–0.8$ (D,L,L form) (ethylacetate).

Step 2:
N-Benzyloxycarbonyl-N-methyl-D-phenylalanyl-L-prolyl-$N^\omega$-benzyloxycarbonyl-DL-arginine-aldehyde 3.41 g (0.005 mole) of N-benzyloxycarbonyl-N-methyl-D-phenylalanyl-L-prolyl-$N^\omega$-benzyloxycarbonyl-DL-arginine lactam (Example 8, Step 1) are transformed according to the procedure described in Example 1, Step 2 by using proportional amounts of reagents and solvents. Yield 2.9 g (75%) of a product containing one mole of cyclohexane.

$R_F^3 = 0.52–0.67$.

$[\alpha]_D^{20} = +32.5°$ (c=1, tetrahydrofuran).

Step 3:
N-Methyl-D-phenylalanyl-L-prolyl-DL-arginine-aldehyde sulfate 2.31 g (0.003 mole) of N-benzyloxycarbonyl-N-methyl-D-phenylalanyl-L-prolyl-$N^\omega$-benzyloxycarbonyl-DL-arginine-aldehyde (Example 8, Step 2) are transformed according to the procedure described in Example 1, Step 3, by using proportional amounts of reagents and solvents. Yield 1.15 g (70%)

$R_F^6 = 0.39–0.47$.

$[\alpha]_D^{20} = -109°$ (c=1, water).

EXAMPLE 9

Preparation of a pharmaceutical composition

The 2-ampoule preparation suitable for 6- and 12-hour intravenous infusion is prepared as follows:

N-Methyl-D-phenylalanyl-L-prolyl-L-arginine-aldehyde sulfate (420 to 840 mg) and human albumin (40 to 80 mg) are submitted to joint freeze-drying. The contents of the freeze-dried ampoule are dissolved in sterile, germ-free isotonic saline solution (100 to 200 ml) of an other ampoule.

What we claim is:

1. A peptide-aldehyde derivative having the formula (I)

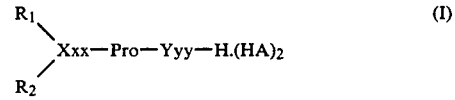

wherein
$R_1$ represents hydrogen or $C_{1-6}$ alkyl group,
$R_2$ stands for $C_{1-6}$ alkyl group, furthermore $R_1$ and $R_2$ are linked to the amino group of the Xxx alpha amino acid,
Xxx represents a D-phenylalanine residue or a D-alloisoleucine residue,
Pro stands for L-proline residue,
Yyy stands for L-, D- or DL-arginine residue, and
A represents an acid residue.

2. A compound according to claim 1, wherein $R_1$ is hydrogen and $R_2$ is a methyl group.

3. A compound according to claim 1, wherein $R_1$ and $R_2$ are methyl groups.

4. A compound of the formula (I) of claim 1, wherein Xxx is a D-phenylalanine residue.

5. A compound of the formula (I) of claim 1, wherein Yyy is an L-arginine residue.

6. A compound of formula (I) as defined in claim 1 selected from the group consisting of N-methyl-D-phenylalanyl-L-prolyl-L-arginine-aldehyde sulfate, N,N-dimethyl-D-phenylalanyl-L-prolyl-L-arginine-aldehyde sulfate, N-ethyl-D-phenylalanyl-L-prolyl-L-arginine-aldehyde sulfate, N-isobutyl-D-phenylalanyl-L-prolyl-L-arginine-aldehyde sulfate, N-methyl-D-alloisoleucyl-L-prolyl-L-arginine-aldehyde sulfate and N-n-hexyl-D-phenylalanyl-L-prolyl-L-arginine-aldehyde sulfate.

7. A pharmaceutical composition having anticoagulant activity, which comprises as active ingredient at least one compound of formula (I) as defined in claim 1 in admixture with one or more pharmaceutical carriers.

8. A method of inhibiting blood coagulation in a mammalian subject which comprises the step of administering to said mammalian subject a therapeutically effective amount of the aldehyde salt of the Formula (I) as defined in claim 1.

9. The method of inhibiting blood coagulation defined in claim 8 wherein the aldehyde salt of the Formula (I) is orally administered to the mammalian subject.

10. The method of inhibiting blood coagulation defined in claim 8 wherein the aldehyde salt of the Formula (I) is intravenously administered to the mammalian subject.

* * * * *